United States Patent
Li et al.

(10) Patent No.: US 6,563,186 B2
(45) Date of Patent: May 13, 2003

(54) HYBRID NANOSTRUCTURED MATERIALS BASED IN II-VI SEMICONDUCTORS

(75) Inventors: Jing Li, Cherry Hill, NJ (US); Xiaoying Huang, Camden, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 10/119,610

(22) Filed: Apr. 10, 2002

(65) Prior Publication Data

US 2002/0149076 A1 Oct. 17, 2002

Related U.S. Application Data

(60) Provisional application No. 60/282,967, filed on Apr. 11, 2001.

(51) Int. Cl.[7] .............................................. H01L 31/00
(52) U.S. Cl. ......................... 257/442; 257/40; 257/642
(58) Field of Search .......................... 257/442, 40, 642

(56) References Cited

U.S. PATENT DOCUMENTS 6,420,056 B1 * 7/2002 Chondroudis et al. ...... 428/690

OTHER PUBLICATIONS

Calvin, et al.—"Light–Emitting Diodes Made from Cadmium Selenide Nanocrystals and a Semiconducting Polymer", Nature, 370, 354–357 (1994), Aug.

* cited by examiner

Primary Examiner—David Nelms
Assistant Examiner—Tu-Tu Ho
(74) Attorney, Agent, or Firm—Synnestvedt & Lechner LLP (57) ABSTRACT

Hybrid crystalline organic-inorganic quantum confined systems are disclosed, which contain alternating layers of a bifunctional organic ligand and a II–VI semiconducting chalcogenide, wherein the semiconducting chalcogenide layers contain chalcogenides have the formula MQ, in which M is independently selected from II–VI semiconductor cationic species and Q is independently selected from S, Se and Te; and the bifunctional organic ligands of each organic ligand layer are bonded by a first functional group to an element M of an adjacent II–VI semiconducting chalcogenide layer and by a second functional group to an element M from the adjacent opposing II–VI semiconducting chalcogenide layer, so that the adjacent opposing II–VI semiconducting chalcogenide layers are linked by the bifunctional organic ligands of the organic ligand layers. Optical absorption experiments show that these systems produce a significant blue shift in their optical absorption edges, 1.2–1.5 eV, compared to a shift of 1.0 electron volt by the best grown II–VI or II–V semiconducting quantum colloidal dots. In addition, the II–VI confined layers in these systems possess a perfectly periodic arrangement.

12 Claims, 10 Drawing Sheets

HYBRID NANOSTRUCTURED MATERIALS BASED IN II-VI SEMICONDUCTORS

This application claims the benefit of Provisional application Ser. No. 60/282,967, filed Apr. 11, 2001.

BACKGROUND OF THE INVENTION

The present invention relates to organic-inorganic hybrid composites which have unique and useful electronic and optical properties. More specifically, the invention relates to II–VI semiconducting chalogenides with modified structures and properties based upon the incorporation of organic components via coordination or covalent bonds.

Group II–VI semiconducting chalcogenide compounds such as CdTe and ZnSe are of great interest currently for use in semiconductor devices because of their relatively wide band gaps. Semiconductor nanostructures with uniform arrangement, such as periodic arrays of quantum dots, are necessary to achieve a sharp line width and strong intensity for practical applications in optoelectronic devices. Quantum dots grown by colloidal methods are highly attractive because of their small size and strong capability for modifying electronic and optical properties of semiconductor bulk materials. For example, InP dots with sizes ranging from two to six nanometers in diameter can shift optical gaps by as much as one electron volt. The great challenge, however, is to generate uniformly sized dots and to organize them into periodic arrays in order to obtain sharp line width, and control over intensity and other optical properties. Self-assembled strain dots have some uniform structures, but their ability to change optical properties is severally limited. This substantially restricts their uses.

There remains a need for quantum confined systems combining uniformity in structure with the ability to significantly modify the electronic and optical properties of semiconducting materials.

SUMMARY OF THE INVENTION

This need is met by the present invention. Applicants have discovered a new type of quantum confined nanostructures that are not only capable of modifying optical, electronic and other properties of a semiconductor on the same large scale as colloidal dots, but also present uniform structures that are particularly advantageous to device making. Compounds of the present invention are covalent or coordinate bonded organic-inorganic hybrid materials with a uniform, periodic nanostructure exhibiting significant quantum confinement effects.

The structures of the hybrid materials of the present invention are constructed in such a way that they contain uniformly sized II–VI semiconductor fragments as sources of the desired semiconductor functionality, and organic spacers as links or nodes to the inorganic fragment motifs in an ordered fashion. The quantum confinements induced in such systems are unusually strong, as a result of highly confined, single-atomic inorganic layers with a thickness less than one nanometer. This leads to a significant blue shift in their optical absorption edges (as high as 1.2–1.5 electron volts), compared to 1.0 electron volt shift obtained by the best-grown III–V and II–VI semiconductor quantum dots.

Therefore, according to one of the embodiment of the present invention, a quantum confined system is provided that is a crystalline organic-inorganic hybrid compound containing alternating layers of a bifunctional organic ligand and a II–VI semiconducting chalcogenide, wherein:

the semiconducting chalcogenide has the formula MQ, in which M represents one or more II–VI semiconductor cationic species and Q is a chalcogen element selected from S, Se or Te; and the bifunctional organic ligands of each organic ligand layer are bonded by a first functional group to an element M of an adjacent II–VI semiconducting chalcogenide layer and by a second functional group to an element M from the adjacent opposing II–VI semiconducting chalcogenide layer so that the adjacent opposing II–VI semiconducting chalcogenide layers are linked by the bifunctional organic ligands of the organic ligand layers.

Among the bifunctional organic ligands, organic diamines are preferred, with organic diamines having the formula R—$(NH_2)_2$ being more preferred, with R being $C_2$–$C_6$ straight-chained or branch, substituted or unsubstituted, saturated or unsaturated aliphatic or cycloaliphatic hydrocarbons.

For purposes of the present invention, quantum confined systems are defined as systems exhibiting electronic confinement in at least one dimension. This includes systems that function as quantum wells by exhibiting electronic confinement in one dimension, systems that function as quantum wires by exhibiting electronic confinement in two dimensions, and systems that function as quantum dots by exhibiting electronic confinement in three dimensions.

Furthermore, II–VI semiconducting chalcogenides are defined according to their well-understood meaning, in which the term chalcogenide is limited to S, Se and Te, and the semiconductor has a zinc blende or wurtzite structure. Cationic species of such semiconductor compounds include Zn, Cd, Hg and Mn.

The quantum confined systems of the present invention are prepared by a method that organizes periodic three-dimensional II–VI semiconductor host lattice segments between organic layers by way of stable coordinate or covalent bonds in an ordered manner. Because the quantum confinement effect induced in the hybrid composite materials of the present inventions is the result of inherent structural properties, the restriction on size distribution is lifted and the synthesis methods of present invention can be used to generate particles of unlimited size, with no effect upon their electronic and optical properties. This is in contrast to the properties of nanoparticles grown by colloidal methods, which depend strongly on particle size, and which are formed via uncorrelated nucleus cores, making it difficult to generate particles with the requisite narrow size distribution and ordered structure.

Therefore, according to another aspect of the present invention, a method is provided for the preparation of the crystalline, covalent or coordinate bonded, organic-inorganic hybrid chalcogenide quantum confined systems of the present invention, in which a mixture is heated containing:

(a) a salt of a II–VI semiconductor cationic species; (b) a chalcogen selected from S, Se and Te; and (c) a bifunctional organic compound capable of covalent or coordinate bonding with the cationic species;

at a temperature effective to form the hybrid chalcogenide, until the hybrid chalcogenide is formed.

The alternating semiconductor and organic layers of the hybrid material of the present invention, prepared by the methods described herein, mimic a superlattice structure. However, unlike the conventional semiconductor superlattices where the band offset introduces only a weak confinement, the insulating organic layer will impose a strong confinement on the semiconductor layer, giving rise to a large variation with respect to the bulk semiconductor properties. In addition, the hybrid organic-inorganic nature of the composites of the present invention provides advantages, features and properties that are important for the miniaturization of electronic and optical devices. Representative features include superior electronic and optical properties, as well as rigidity and stability provided by the inorganic component, and high processibility, flexibility, weight reduction and structural diversity provided by the organic component. Therefore, according to another aspect of the present invention, a semiconductor device is provided containing multiple layers of the crystalline organic-inorganic hybrid compounds of the present invention. The semiconductor devices of the present invention are fabricated by known techniques.

As can be appreciated by one skilled in the art, variation of the II–VI semiconducting chalcogenide and bifunctional organic compounds will provide a broad range of hybrid compounds exhibiting a wide range of properties

DETAILED DESCRIPTION OF THE PREFERRED EMBODIMENTS

The inorganic portion of the hybrid compounds of the present invention is a II–VI semiconducting chalcogenide having the formula MQ, where M is a II–VI semiconductor cationic species and Q is a chalcogen selected from S, Se and Te. M is preferably selected from among the above-listed cationic species, and more preferably, M is Zn or Cd. Q is a chalcogen selected from S, Se and Te. Q is preferably Se or Te.

As noted above, the bifunctional organic ligand is preferably an organic diamine having the structure R—(NH$_2$)$_2$, wherein R a $C_2$–$C_6$ straight-chained or branched, substituted or unsubstituted, saturated or unsaturated, aliphatic or cycloaliphatic hydrocarbon. Particularly preferred organic diamines are ethylenediamine and 1, 3-propanediamine.

The hybrid compounds of the present invention are prepared by the reaction of metal salts of one or more II–VI semiconductor cationic species, for example, a halide, sulfate or nitrate salt, with one or more chalcogen elements selected from S, Te and Se, optionally in the form of A$_2$Q (A=alkali metal, Q=S, Se or Te). Preferred cationic species include Zn and Cd. The metal salt and the chalcogen are reacted in the presence of the bifunctional organic compounds, with the molar ratio of metal to chalcogen being between about 4:1 and about 1:1. Preferably, the molar ratio is between about 2:1 and about 1:1.

The bifunctional organic compounds may serve the dual functions of solvent and reactant. However, the invention also encompasses methods wherein an inert solvent such as water, dimethylformamide, and the like are employed. In a preferred embodiment, the bifunctional organic compound serves as reactant and solvent wherein the molar ratio of metal salt to chalcogen to bifunctional organic compound is a ratio between about 2:1:5 and about 2:1:600.

Selected changes in the molar proportions of reactants provide desired changes in the chemical and/or physical properties of the inventive compounds, including, for example, the thickness of the hybrid structure, the selection for which is readily understood by those skilled in the art. In a preferred embodiment in which the bifunctional organic compound functions as both reactant and solvent, the molar proportion of the bifunctional organic compound is about 5 to 600 times that of the amount of chalcogen employed.

The compounds of the present invention are prepared in closed or sealed vessel, such as a stainless steel acid digestion bomb. The reactions are carried out under an elevated pressure of about three to four atmospheres up to about 100 atmospheres.

Suitable reaction temperatures range from 100° to about 220° C., and preferably from about 120° to about 180° C., and the reaction period is suitably from about one to ten days.

Solid products are collected by conventional means, washed free of starting materials and impurities with appropriate solvents such as alcohol-water, and then dried with an anhydrous solvent such as ethyl ether.

In an alternative embodiment, the II–VI semiconductor chalcogenide component is provided as a precursor which is reacted directly with the bifunctional organic compounds at elevated temperatures and pressure to form the compounds of the present invention. For example, the II–VI semiconducting chalcogenide can be reacted with ethylenediamine or 1, 3-propanediamine at 200° C. for three days.

The compounds of the present invention may be configured into structures that are useful in the fabrication of electrical and optical devices by conventional means. For example, the compounds of the present invention may be formed into structures that function as quantum dots, quantum wells and quantum wires. Generally speaking, the compounds of the present invention will find applications in devices where these quantum confined structures are useful. These include, but are not limited to, interlayer dielectric devices in microelectronics, thermoelectric devices for cooling, beating and generating electricity, and quantum well laser structures useful in optoelectric devices for the generation or modulation of light radiation, including the modulation of light radiation for the transmission of information. The semiconductor compounds of the present invention may also be used in infra-red photodetectors, lasers for spectroscopic and fiber optic applications, electroluminescent lasers and electronic phosphors.

The following non-limiting examples set forth hereinbelow illustrate certain aspects of the invention. All parts and percentages are molar unless otherwise noted and all temperatures are in degrees Celsius.

EXAMPLES

Materials and Instruments. $MnCl_2$ (97%, Alpha Aesar), $ZnCl_2$ (98%, Aldrich), $Zn(NO_3)_2 \cdot 6H_2O$ (99.7%, Fisher), Se (99.5%, Strem), Te (99.8%, Strem), ethylenediamine (99%, anhydrous, Aldrich), and 1, 3-propanediamine (98%, anhydrous, Alfa Aesar) were used as received without further purification. Powder X-Ray Diffraction (PXRD) of samples was performed on a Rigaku D/M-2200T automated diffraction system (Ultima+). The structure analyses were carried out using JADE (Windows) and GSAS software packages. The calculated PXRD patterns were generated from the single crystal data. Optical diffuse reflectance spectra were measured at room temperature with a Shimadzu UV-3101PC double beam, double monochromated spectrophotometer. Thermogravimetric analyses (TGA) were performed on a computer controlled TA Instrument TGA-2050 system.

Example 1

Preparation of $[\alpha\text{-ZnTe(Ethylenediamine)}_{1/2}]$ I

To a 23 mL acid digestion bomb was charged 0.272 g $ZnCl_2$ (2 mmol), 0.128 g Te (1 mmol) and 6 mL ethylenediamine. The mixture was allowed to react at 200° C. for a period of three days. A solid product was collected, washed with 30 and 80% ethanol, and then dried in anhydrous ethyl ether giving brownish column-like crystals of the title compound in 90.0% yield.

Example 2

Preparation of $[\beta\text{-ZnTe(Ethylenediamine)}_{1/2}]$ II

A reaction mixture of 0.595 g $Zn(NO_3)_2 \cdot 6H_2O$ (2 mmol), 0.128 g Te (1 mmol), and ethylenediamine (6 mL, 90 mmol) was heated in a 23 mL acid digestion bomb at 190° C. for three days. A solid product was collected, washed with 30 and 80% ethanol, and dried in anhydrous ethyl ether, affording brownish platelike crystals of the title compound (92.4% yield).

Example 3

Preparation of $[\text{ZnTe(1,3-Propanediamine)}_{1/2}]$ III

The title compound was prepared as in Example 2 with the exception that 1,3-propanediamine (5 mL, 60 mmol) was used in place of ethylenediamine and the reaction temperature was 200° C. The title compound was obtained in 91.3% yield.

Example 4

Preparation of $[\text{MnSe(Ethylenediamine)}_{1/2}]$ IV

Single crystals of IV were obtained by the solvothermal reaction of 0.063 g $MnCl_2$ (0.50 mmol) and 0.020 g Se (0.25 mmol). The starting materials were weighed and mixed, and then transferred to a thick-walled Pyrex tube, after which 0.4 mL ethylenediamine was added. After the liquid was condensed by liquid nitrogen, the tube was sealed with a torch under vacuum (about $10^{-3}$ Torr). The sample was then heated at 160° C. for seven days. After being cooled to room temperature, the mixture was washed with 30% and 80% ethanol followed by drying in anhydrous ethyl ether. Orange-reddish plate-like crystal (0.040 g, 96.3% yield based on Se) of IV were obtained.

Example 5

Preparation of $[\text{MnSe(1, 3-Propanediamine)}_{1/2}]$ V

The reaction of $MnCl_2$(0.0310 g, 0.25 mmol), Se (0.020 g, 0.25 mmol) and 1, 3-propanediamine (0.4 mL) in an molar ratio of 1:1:19 at 125° C. for twelve days in thick-walled Pyrex tubes afforded orange plate-like crystals of V (0.031 g, 71.6% yield based on Se). The same experimental procedure used for the synthesis of IV was applied here.

Example 6

Preparation of $[\text{ZnSe(Ethylenediamine)}_{1/2}]$ VI

Compound VI was obtained from the reaction of $ZnCl_2$ (0.273 g, 2 mmol), Se (0.079 g, 1.0 mmol) and ethylenediamine (5.0 mL) in a molar ratio of 2:1:75 in a 23 mL acid digestion bomb at 140° C. for eight days. The product was washed with 30% ethanol and water followed by drying in anhydrous ethyl ether. A tan powder of VI (0.155 g, 88.9% yield based on Se) was isolated.

Example 7

Preparation of $[\text{ZnSe(1, 3-propanediamine)}_{1/2}]$ VII

Compound VII was prepared from the reaction of $ZnCl_2$ (0.273 g, 2.0 mmol), Se (0.079 g, 1.0 mmol) and 1, 3-propanediamine (6.0 mL) in a molar ratio of 2:1:75 in a 23 mL acid digestion bomb at 140° C. for eight days. The product was washed with 30% ethanol and water followed by drying in anhydrous ethyl ether. A tan powder of VII (0.130 g, 71.7% yield based on Se) was isolated.

CRYSTAL STRUCTURE OF I–VII

Figure 1A:
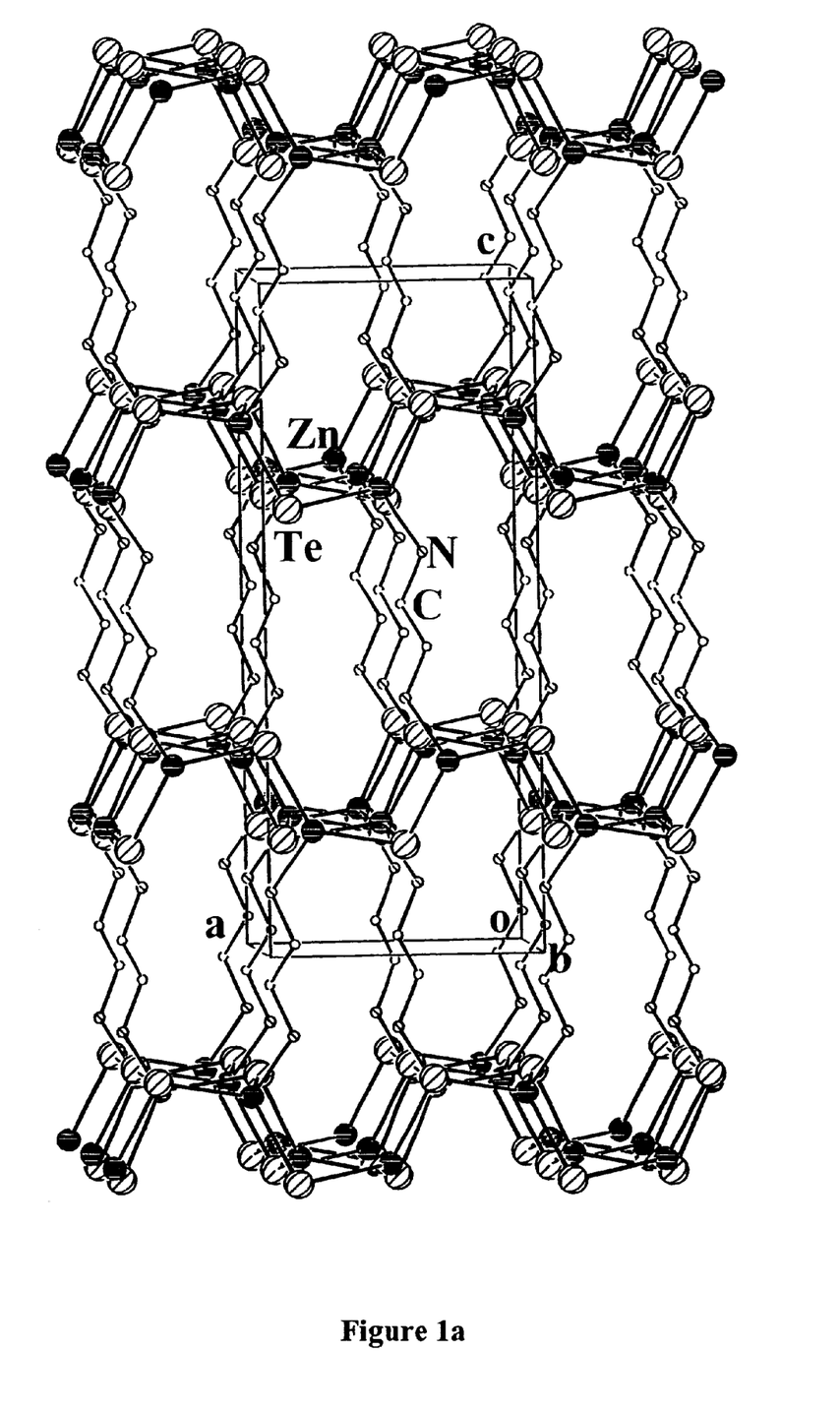
FIG. 1a is a diagrammatic representation of the crystal structure of [α-ZnTe(ethyl-enediamine)$_{1/2}$] (I) shown along the b-axis.
Figure 1B:
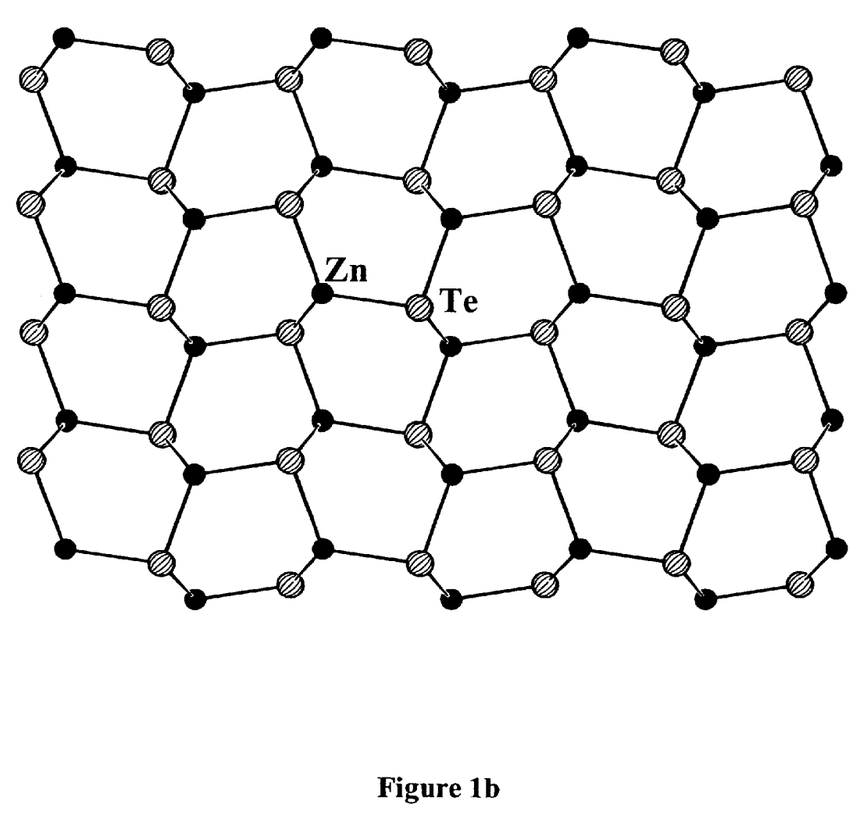
FIG. 1b is a diagrammatic representation of the inorganic slab in I shown along the c-axis.
Figure 2A:
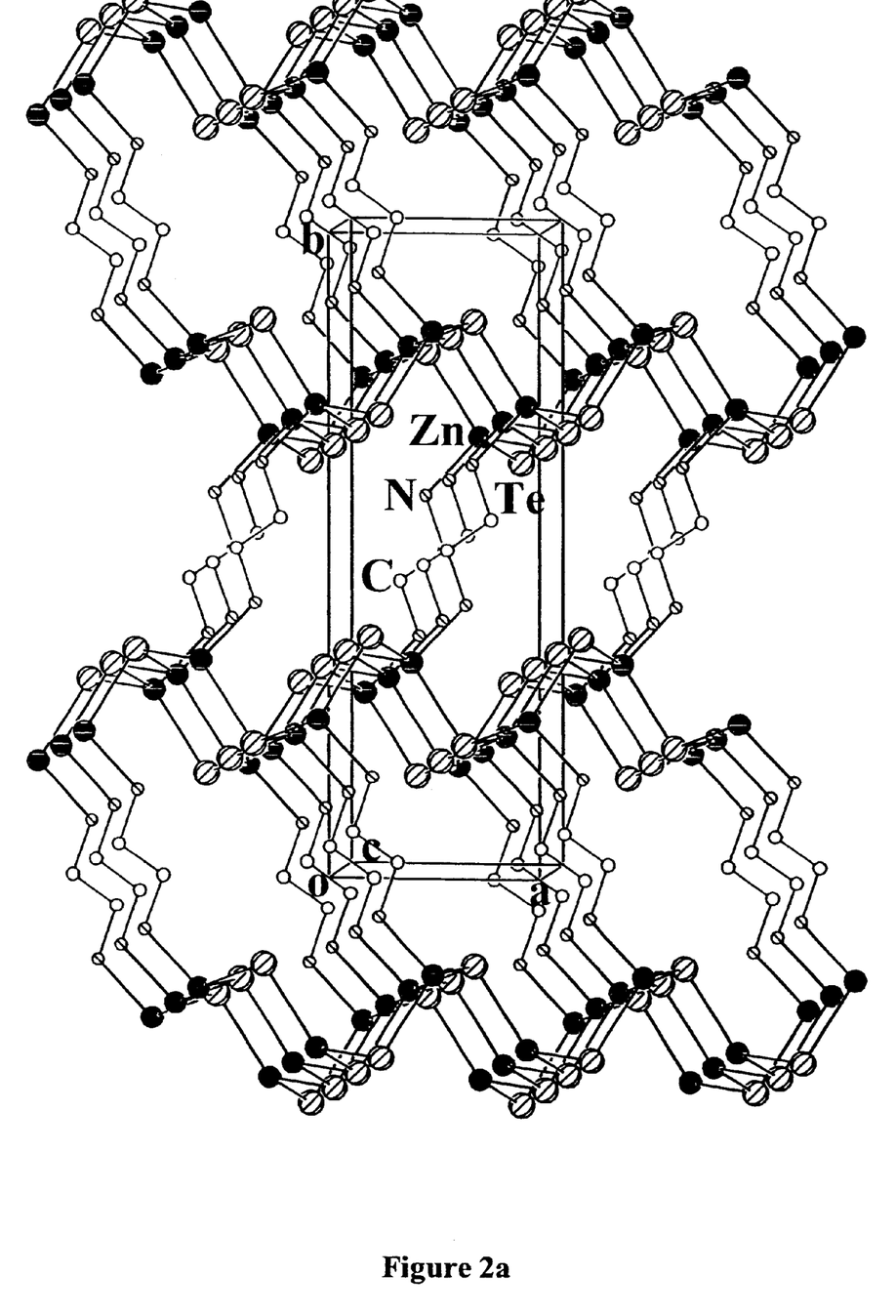
FIG. 2a is a diagrammatic representation of [β-ZnTe (ethylenediamine)$_{1/2}$] (II) shown along the c-axis.
Figure 2B:
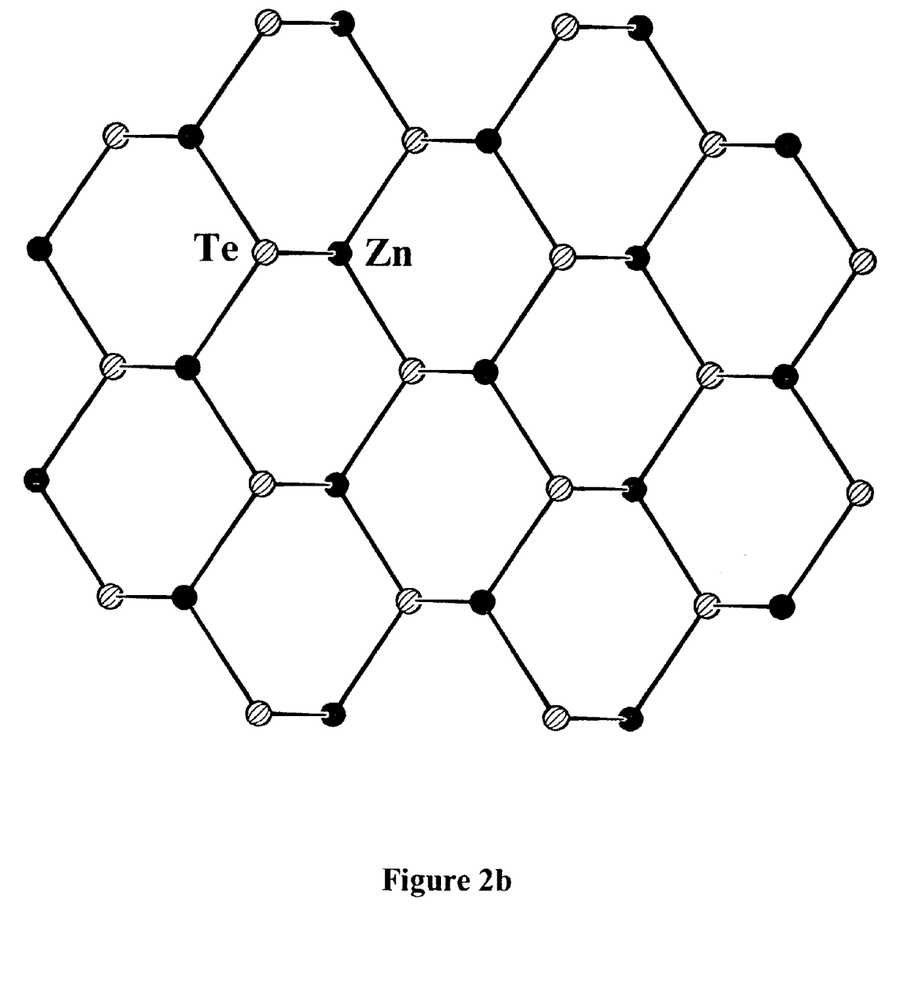
FIG. 2b is a diagrammatic representation of the inorganic slab in II shown along the b-axis.

Single crystal X-ray diffraction analysis of compound I revealed a crystal structure of a three-dimensional network containing inorganic monolayers of ZnTe that are interconnected by bridging ethylene diamine molecules. The inorganic slab of each monolayer is in the form of a honeycomb network of Zn and Te interconnected by coordinate bonds to the organic spacer, ethylenediamine (see FIG. 1). The slab can also be regarded as a slice cut from the parent zinc blende or wurtzite-type structure of ZnTe. Each Zn atom within the slab achieved a stable tetrahedral configuration through four bonds, three with adjacent Te atoms and the fourth with a nitrogen atom of the ligand bridge as shown in FIGS. 1a and 1b. The compound $[\beta\text{- ZnTe(ethylenediamine)}_{1/2}]$ II is a polymorph of I. Its crystal structure is depicted in FIG. 2.

Figure 4A:
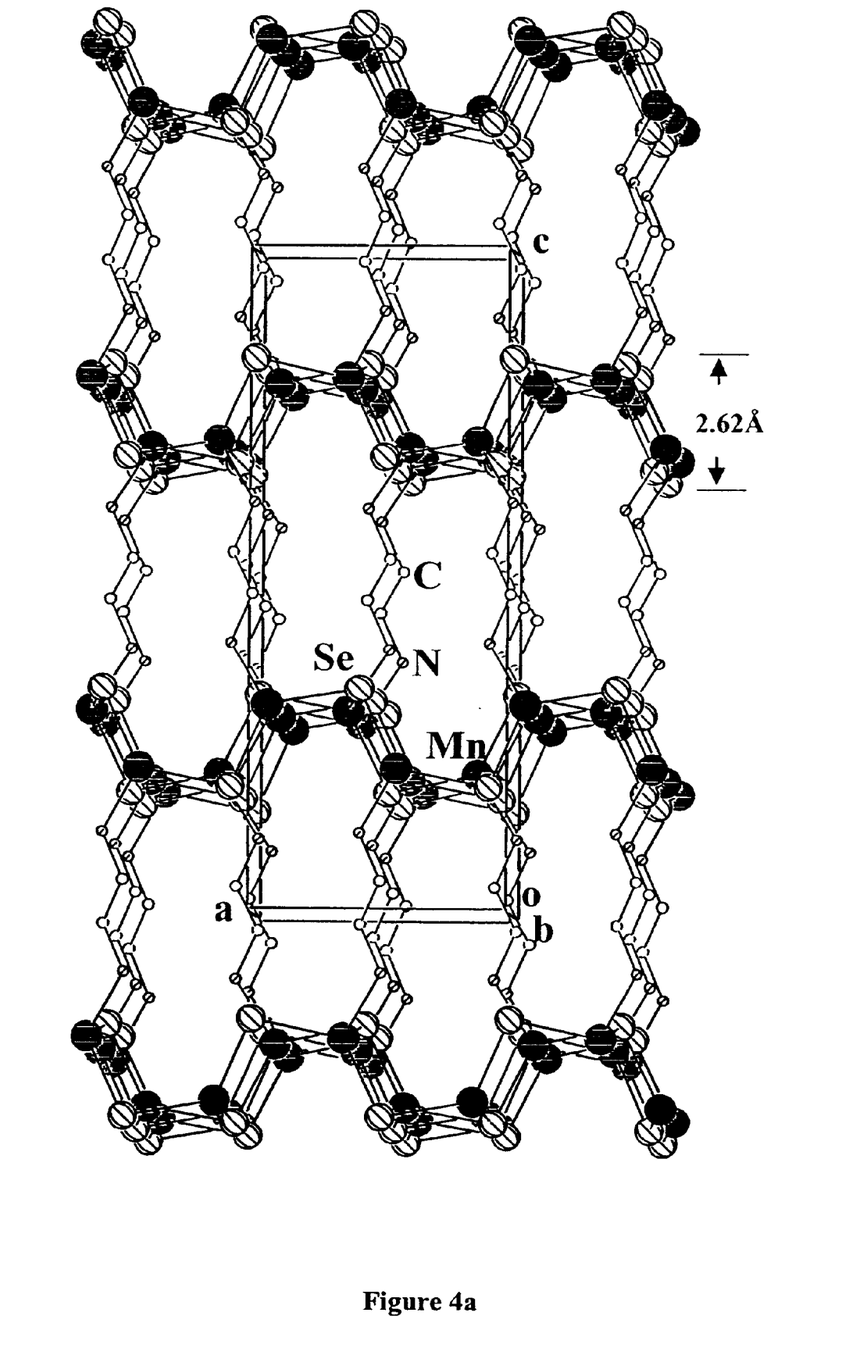
FIG. 4a is a diagrammatic representation of the crystal structure of [MnSe(ethyl-enediamine)$_{1/2}$] (IV) shown along the b-axis.
Figure 4B:
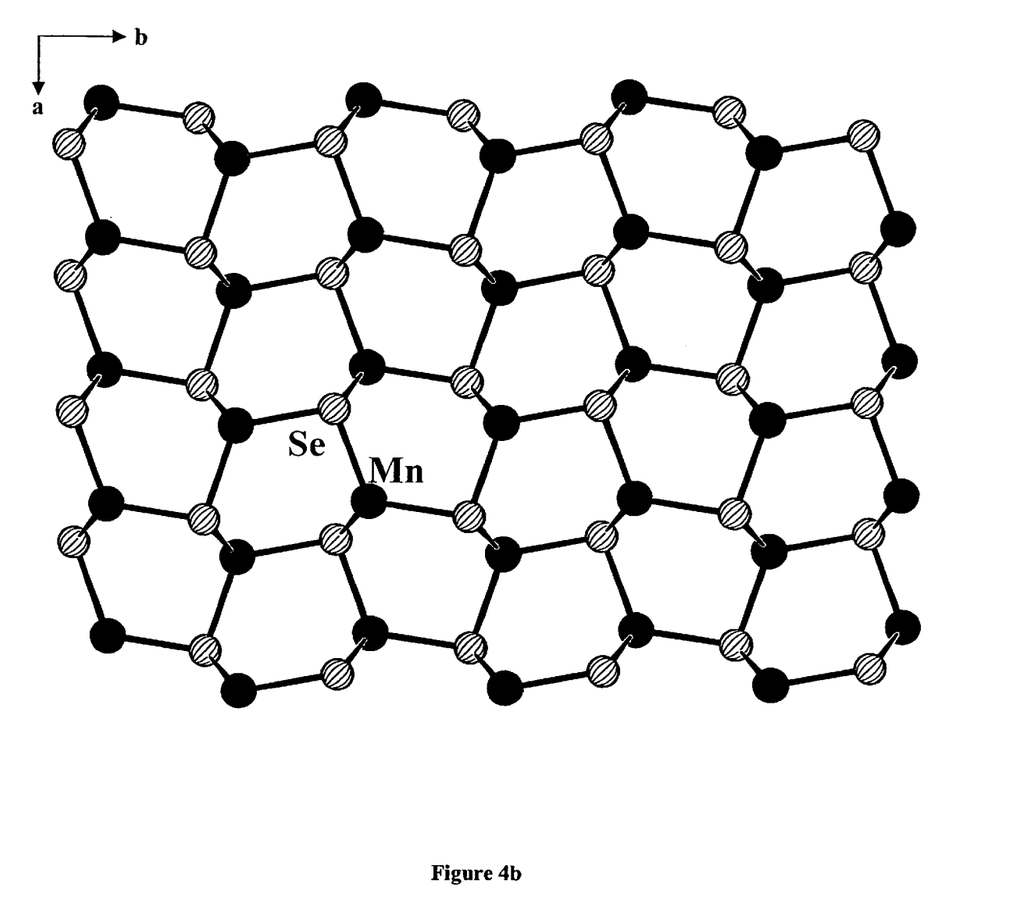
FIG. 4b is a diagrammatic representation of the inorganic slab in IV shown along the c-axis.
Figure 5A:
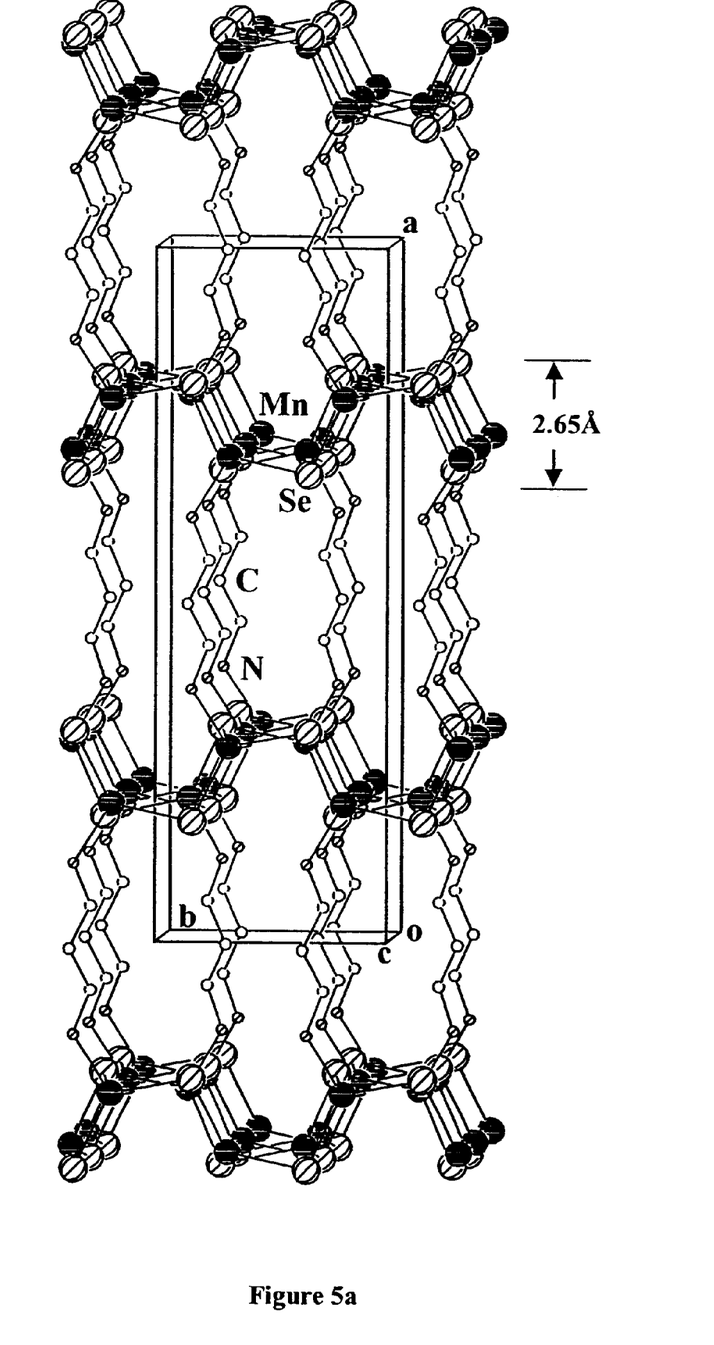
FIG. 5a is a diagrammatic representation of the crystal structure of [MnSe(1,3-propanediamine)$_{1/2}$] (V) shown along the c-axis.
Figure 5B:
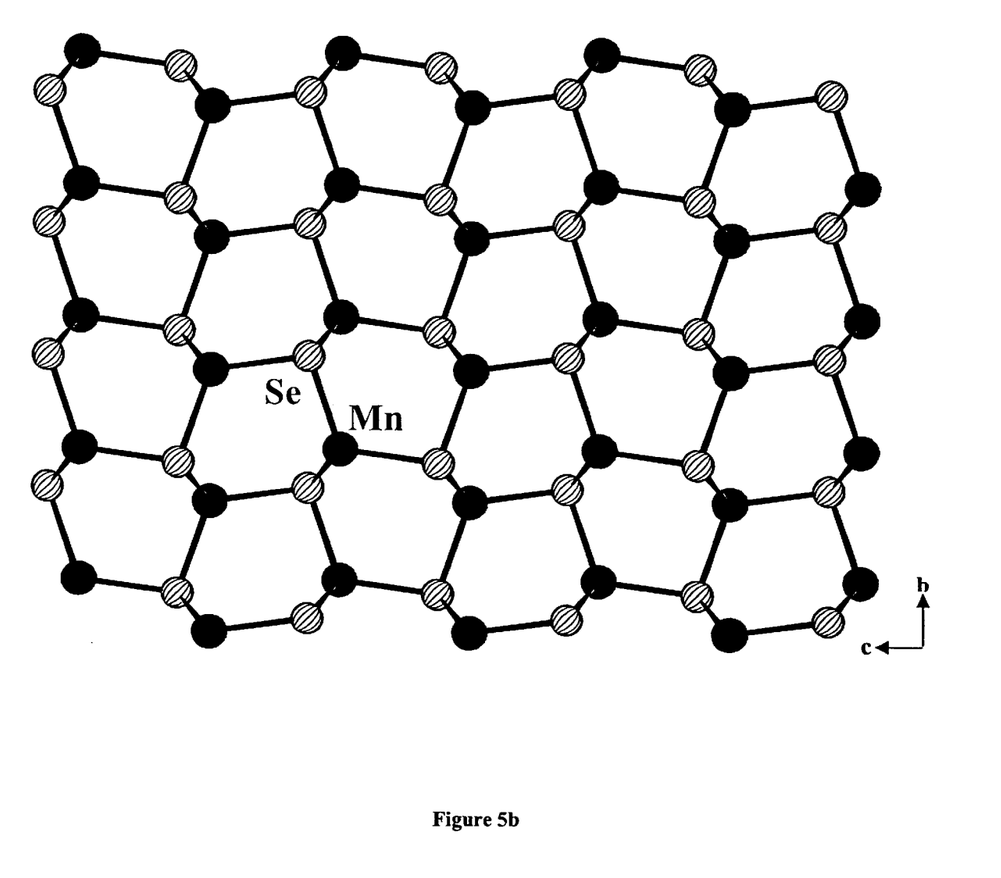
FIG. 5b is a diagrammatic representation of the inorganic slab in V shown along the a-axis.

Compound IV is isostructural to I. FIG. 4a illustrates a view of IV along the b-axis. Structure V is isostructural to III. As depicted in FIG. 5, the inorganic slabs in IV and V are almost identical in the two structures. The only difference is in the organic pillars, with ethylenediamine in IV and 1, 3-propanediamine in V. Compounds VI and VII are isostructural to I (and IV), and III (and V) respectively. The MSe slabs (M=Mn, Zn) have a thickness that falls well below the nanometer regime (e.g. 0.262 and 0.265 nm for IV and V, respectively). In fact this thickness is at a single atomic monolayer, the smallest possible length scale that can be achieved by a quantum confined II–VI system. These highly correlated, yet well separated nanometer-sized semiconductor fragments thus represent an unprecedented type of nanostructure with a very strong quantum confinement effect.

OPTICAL ABSORPTION SPECTROSCOPY

Figure 3:
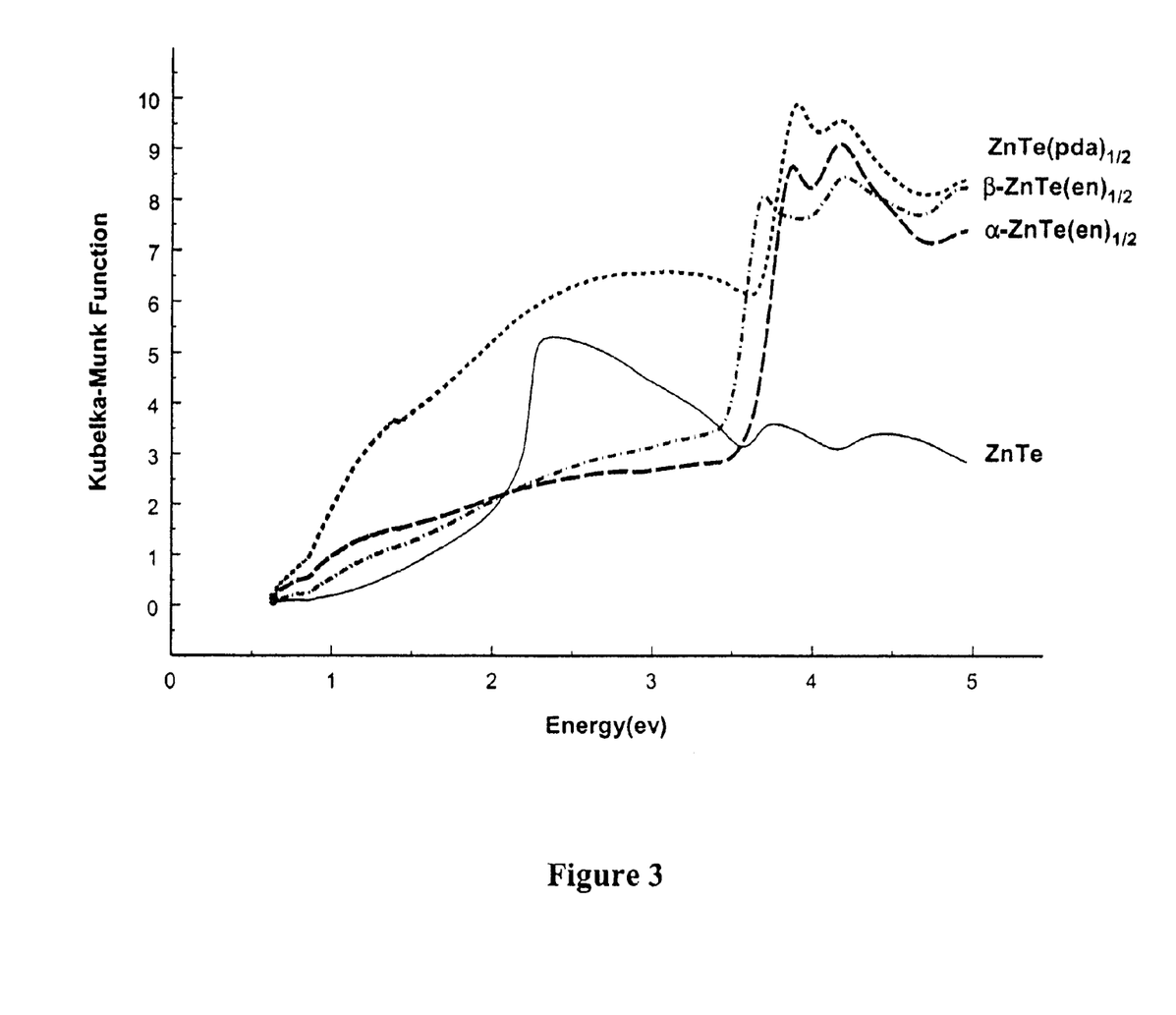
FIG. 3 is a graphic depiction of the optical absorption spectra of compounds I, II, ZnTe(1,3-propanediamine)$_{1/2}$] (III) and bulk ZnTe.

The optical absorption spectra of compounds I, II and III were compared graphically in FIG. 3 with the spectrum of bulk ZnTe. The analyses were conducted by diffuse reflectance using a Shimadzu UV-3101 PC double-beam, double monochromator spectrophotometer. The results show a substantial blue shift of 1.2–1.4 eV for the three hybrid compounds as compared to bulk ZnTe.

Figure 6:
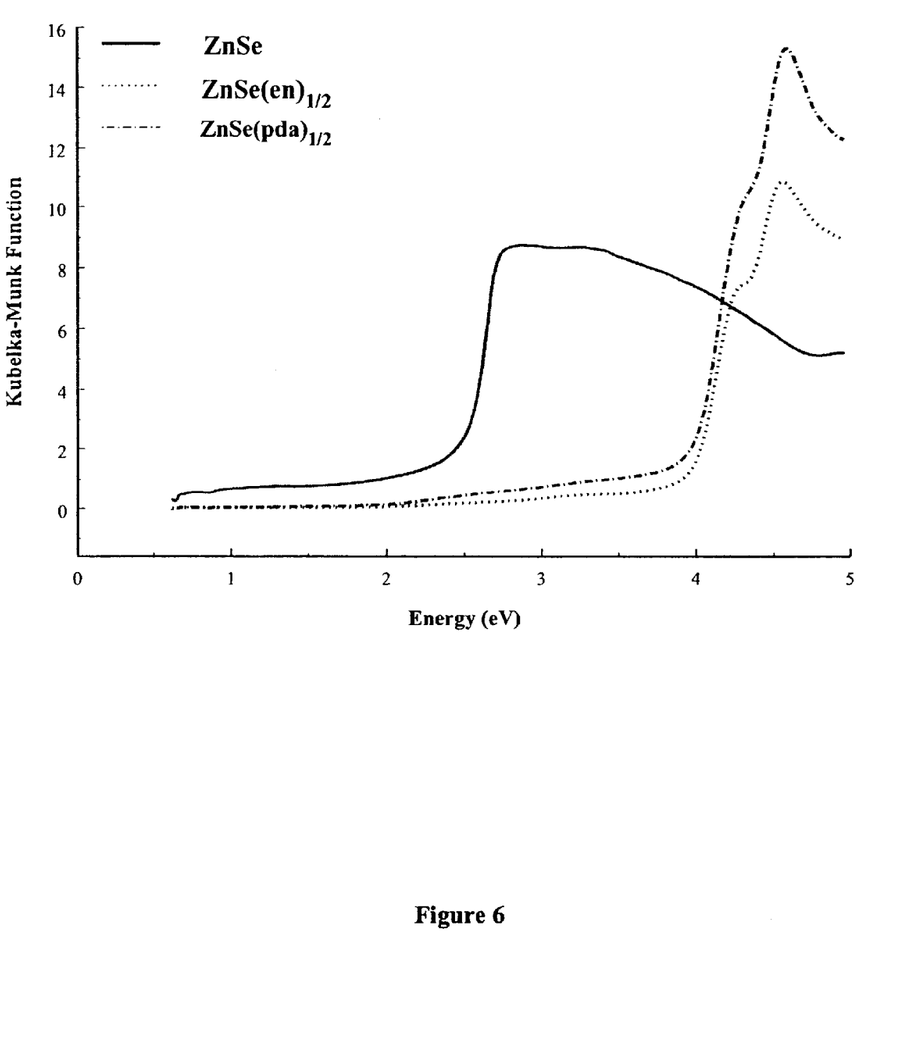
FIG. 6 is a graphic depiction of the optical absorption spectra of [ZnSe(ethyl-enediamine)$_{1/2}$] (VI, dotted line), [ZnSe (1,3-propanediamine)$_{1/2}$] (VII, doffed dash), and bulk ZnSe(Stilleite, solid line).

The optical absorption spectra of VI and VII were measured by the same experimental method, with the results depicted in FIG. 6, along with that of ZnSe(Stilleite). The absorption edges for VI and VII are found to be 4.0 and 3.9 eV, respectively. Compared to the measured value of 2.5 eV for ZnSe(Stilleite), it clearly indicates a very large blue shift (1.4–1.5 eV), one that has not been achieved by any chemically grown colloidal dots. The optical properties of IV and V were also assessed by the same experiments conducted at room temperature. The estimated absorption edges are 1.8 and 1.7 eV for IV and V, respectively, compared to about 1.6 eV measured for the α-MnSe bulk sample (NaCl structure). Note that this value is somewhat smaller than the previously reported $E_g$ for MnSe. While ZnSe and ZnTe-based hybrid compounds (I–III, VI, VII) exhibit significant changes (1.2–1.5 eV) in their optical absorption edge, it is noted that IV and V give rise to changes in the same direction (increase in energy) with respect to bulk MnSe, but to a much smaller extent (0.1–0.2 eV). This is attributable to the Mn 3d bands that are highly localized and, therefore, the quantum confinement induced by organic spacers via coordinate bonds leads to a much smaller variation in these bands.

THERMAL PROPERTIES

The thermogravimetic analyses were performed on polycrystalline samples of VI and VII. Both compounds underwent a single-step weight loss process and were thermally stable up to 250° C. The measured weight losses of the organic species are 17.7% (2.006 mg) for ethylenediamine (VI) and 21.9% (2.270 mg) for 1, 3-propanediamine (VII), respectively, in excellent agreement with the calculated values, 17.3% for ethylenediamine and 20.4% for 1, 3-propanediamine, respectively. The decomposition process completed at approximately 400° C. for both VI and VII. Powder X-ray diffraction analysis immediately following the thermogravimetric experiments showed that the residues of both samples contained two isomorphic phases of ZnSe, with the major phase being wurtzite structure (P6₃mc) and the minor one, zinc blende structure (F 4 3 m, Stilleite). The optical diffuse reflectance measurement gave an estimated band gap of about 2.7 eV for ZnSe of the wurtzite structure, indicating a small blue shift of 0.2 eV with respect to ZnSe of the zinc blende structure.

The foregoing examples demonstrate that an unprecedented type of nanostructure with both strong quantum confinement and periodic arrangement can be synthesized in high yield. Other II–VI semiconductors have also been determined to form the same type of hybrids with strong quantum confinement effects being a general phenomenon in the systems. The quantum confined systems of the present invention are particularly advantageous because the electrons are confined within the thin semiconductor slabs by coordinated organic spacers, which direct and organize the semiconductor slab into an ordered, crystalline three-dimensional lattice rather than be uncorrelated nanoparticles as in the case of colloidal dots. Because such confinements are induced internally as a consequence of inherent structural properties, there is no dependence upon particle size. Consequently, new hybrid nanostructures can be prepared by means of ordinary synthetic routes without limitation or restriction on their physical dimensions, in contrast to quantum dots to which size distribution directly effects performance. This uniformity in structure and the capability for modification of material properties makes the hybrid materials of the present invention ideal materials for new-generation nanodevices.

Numerous variations and combinations of the features described above can be utilized without departing from the invention. For example, modifications in the II–VI semiconductor bulk structure have been explored by varying the thickness of inorganic slabs (n) between the organic ligand layers. While the strongest quantum confinement effect was achieved at n=1, synthesis of hybrid structures having n greater than one allow a controllable tuning of electronic electrical properties. The foregoing examples and description of the preferred embodiment should be taken as illustrating, rather than as limiting the present invention as defined by the claims.

We claim:

1. A hybrid crystalline organic-inorganic quantum confined system comprising alternating layers of bifunctional organic ligands and II–VI semiconducting chalcogenides, wherein:
   the semiconducting chalcogenide layer comprises II–VI chalcogenides having the formula MQ, in which each M is independently selected from the group consisting of II–VI semiconductor cationic species, and each Q is independently selected from the group consisting of S, Se and Te; and
   said bifunctional organic ligands of each organic ligand layer are bonded by a first functional group to an element M of an adjacent II–VI semiconducting chalcogenide layer and by a second functional group to an element M from the adjacent opposing II–VI semiconducting chalcogenide layer, so that said adjacent opposing I–VI semiconducting chalcogenide layers are linked by said bifunctional organic ligands of said organic ligand layers.

2. The quantum confined system of claim 1, wherein M of said hybrid compound is Zn or Cd.

3. The quantum confined system of claim 1, wherein Q of said hybrid compound is Se or Te.

4. The quantum confined system of claim 1, wherein the bifunctional organic ligand of said of hybrid compound is an organic diamine having the formula R—(NH₂)₂, wherein R is a C₂–C₆ straight-chained or branched, substituted or unsubstituted, saturated or unsaturated, aliphatic or cycloaliphatic hydrocarbon.

5. The quantum confined system of claim 4, wherein said diamine of said hybrid compound is ethylenediamine or 1, 3-propanediamine.

6. The quantum confined system of claim 1, further comprising additional II–VI semiconducting chalcogenide layers between adjacent opposing bifunctional organic ligand layers.

7. A semiconductor device comprising the quantum confined system of claim 1.

8. A method for the preparation of a crystalline organic-inorganic hybrid quantum confined system comprising plural alternating layers of a bifunctional organic ligand and II–VI semiconducting chalcogen, said method comprising the step of heating a mixture comprising;
   (a) a salt of one or more II–VI semiconductor cationic species; (b) one or more chalcogens selected from the group consisting of S, Se and Te; and (c) a bifunctional organic compound capable of forming covalent or coordinate bond with said II–VI semiconductor cationic species;

at a temperature effective to form said hybrid compound, until said hybrid compound is formed.

9. A method according to claim 8, wherein said salt is a salt of Zn or Cd.

10. The method of claim 8, wherein said chalcogen is Se or Te.

11. The method of claim 8, wherein said bifunctional organic compound is an organic diamine having the formula R—$(NH_2)_2$, wherein R is a $C_2$–$C_6$ straight-chained or branched, substituted or unsubstituted, saturated or unsaturated, aliphatic or cycloaliphatic hydrocarbon.

12. The method of claim 11, wherein said organic diamine is ethylenediamine or 1, 3-propanediamine.

* * * * *

UNITED STATES PATENT AND TRADEMARK OFFICE
CERTIFICATE OF CORRECTION

PATENT NO. : 6,563,186 B2  Page 1 of 1
DATED : May 13, 2003
INVENTOR(S) : Jing Li and Xiaoying Huang It is certified that error appears in the above-identified patent and that said Letters Patent is hereby corrected as shown below:

Column 8,
Line 38, after the word "opposing" replace "I-VI" with -- II-VI --.

Signed and Sealed this

Seventh Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,563,186 B2
DATED : May 13, 2003
INVENTOR(S) : Jung Li and Xiaoying Huang Page 1 of 1

It is certified that error appears in the above-identified patent and that said Letters Patent is hereby corrected as shown below:

<u>Column 1,</u>
Line 6, insert
-- GOVERNMENT SUPPORT
   The development of this invention was supported in part by National Science Foundation Grant DMR-0094872. The Government has certain rights in the invention. --

Signed and Sealed this

Tenth Day of May, 2005

JON W. DUDAS
*Director of the United States Patent and Trademark Office*